(12) United States Patent
Wataya et al.

(10) Patent No.: US 9,872,611 B2
(45) Date of Patent: Jan. 23, 2018

(54) IMAGE PICKUP UNIT AND ENDOSCOPE

(71) Applicant: OLYMPUS CORPORATION, Tokyo (JP)

(72) Inventors: Yuichi Wataya, Akiruno (JP); Akira Muramatsu, Musashino (JP); Yukiharu Makino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/633,970

(22) Filed: Jun. 27, 2017

(65) Prior Publication Data

US 2017/0296044 A1    Oct. 19, 2017

Related U.S. Application Data

(63) Continuation of application No. PCT/JP2016/061764, filed on Apr. 12, 2016.

(30) Foreign Application Priority Data

Aug. 5, 2015   (JP) .................................. 2015-155370

(51) Int. Cl.
*G02B 15/14* (2006.01)
*A61B 1/05* (2006.01)
*A61B 1/00* (2006.01)
*H04N 5/225* (2006.01)

(52) U.S. Cl.
CPC ............ *A61B 1/05* (2013.01); *A61B 1/00096* (2013.01); *H04N 5/2254* (2013.01); *A61B 1/0011* (2013.01); *H04N 5/2256* (2013.01)

(58) Field of Classification Search
CPC ..... A61B 1/05; A61B 1/00096; A61B 1/0011; H04N 5/2254; H04N 5/2256

USPC .................................................. 359/691, 692
See application file for complete search history.

(56) References Cited

U.S. PATENT DOCUMENTS

2007/0118019 A1   5/2007  Mitani et al.

FOREIGN PATENT DOCUMENTS

| EP | 1769719 A1 | 4/2007 |
|---|---|---|
| EP | 2218391 A1 | 8/2010 |
| JP | S61-107307 A | 5/1986 |
| JP | 2000-304992 A | 11/2000 |
| JP | 2003-230532 A | 8/2003 |
| JP | 2006-015076 A | 1/2006 |
| JP | 2008-253789 A | 10/2008 |
| JP | 2012-120774 A | 6/2012 |

(Continued)

OTHER PUBLICATIONS

International Search Report dated Jul. 19, 2016 issued in PCT/JP2016/061764.

*Primary Examiner* — Jack Dinh
(74) *Attorney, Agent, or Firm* — Scully, Scott, Murphy & Presser, P.C.

(57) ABSTRACT

An image pickup unit, includes: a front group lens frame holding a front group lens; a rear group lens frame fitted to the front group lens frame and holding a rear group lens; a movable frame disposed to be movable forward and backward in a direction along a photographing optical axis within the rear group lens frame, and holding a movable lens; an adhesive bonding the front group lens frame to the rear group lens frame; and an adhesive outflow preventing portion preventing the adhesive from flowing out toward the movable frame side when the front group lens frame is bonded and fitted to the rear group lens frame.

9 Claims, 13 Drawing Sheets

(56) References Cited

FOREIGN PATENT DOCUMENTS

| JP | 5374669 B1 | 12/2013 |
|---|---|---|
| WO | WO 2006004123 A1 | 1/2006 |
| WO | WO 2013/128681 A1 | 9/2013 |

IMAGE PICKUP UNIT AND ENDOSCOPE

CROSS REFERENCE TO RELATED APPLICATION

This application is a continuation application of PCT/JP2016/061764 filed on Apr. 12, 2016 and claims benefit of Japanese Application No. 2015-155370 filed in Japan on Aug. 5, 2015, the entire contents of which are incorporated herein by this reference.

BACKGROUND OF THE INVENTION

1. Field of the Invention

The present invention relates to an image pickup unit that makes it possible to change optical characteristics of an observation optical system, and to an endoscope provided with the image pickup unit.

2. Description of the Related Art

As is well known, an endoscope is widely used for observation, treatment, and the like in-vivo (in a body cavity), and for inspection, repair and the like of an industrial plant facility.

In recent years, some of such kinds of endoscopes may use an image pickup unit that moves an observation optical system in a photographing optical axis direction to vary a focal length for a zooming function of adjusting focus of a photographed image or adjusting magnification such as wide and tele. Note that the technology of the image pickup unit that can vary the focal length as mentioned above is used in various photographing apparatuses without being limited to the endoscope.

For example, as disclosed in Japanese Patent Application Laid-Open Publication No. 2003-230532, an image pickup apparatus for an endoscope that is an image pickup unit in which a movable lens frame slides, in an optical direction, inside a rear group lens frame fitted to a front group lens frame to vary optical characteristics is known.

An existing image pickup unit suppresses a size of a clearance between components as much as possible by reducing process balance of the components, thereby guaranteeing image quality after the front group lens frame and the rear group lens frame are assembled.

SUMMARY OF THE INVENTION

An image pickup unit according to an aspect of the present invention, includes: a front group lens frame holding a front group lens; a rear group lens frame fitted to the front group lens frame and holding a rear group lens; a correction frame fixed within the rear group lens frame; a movable frame disposed to be movable forward and backward in a direction along a photographing optical axis within the correction frame, and holding a movable lens; a stopper provided in the correction frame, the stopper restricting movement of the movable frame in one direction of the photographing optical axis by coming into contact with the movable frame, to achieve one of focal lengths of an observation optical system; an adhesive bonding the front group lens frame to the rear group lens frame; and an adhesive outflow preventing portion preventing the adhesive from flowing out toward the movable frame side.

In addition, an endoscope according to an aspect of the present invention includes an image pickup unit, and the image pickup unit includes: a front group lens frame holding a front group lens; a rear group lens frame fitted to the front group lens frame and holding a rear group lens; a correction frame fixed within the rear group lens frame; a movable frame disposed to be movable forward and backward in a direction along a photographing optical axis within the correction frame, and holding a movable lens; a stopper provided in the correction frame, the stopper restricting movement of the movable frame in one direction of the photographing optical axis by coming into contact with the movable frame, to achieve one of focal lengths of an observation optical system; an adhesive bonding the front group lens frame to the rear group lens frame; and an adhesive outflow preventing portion preventing the adhesive from flowing out toward the movable frame side.

DETAILED DESCRIPTION OF THE PREFERRED EMBODIMENT(S)

Figure 1:
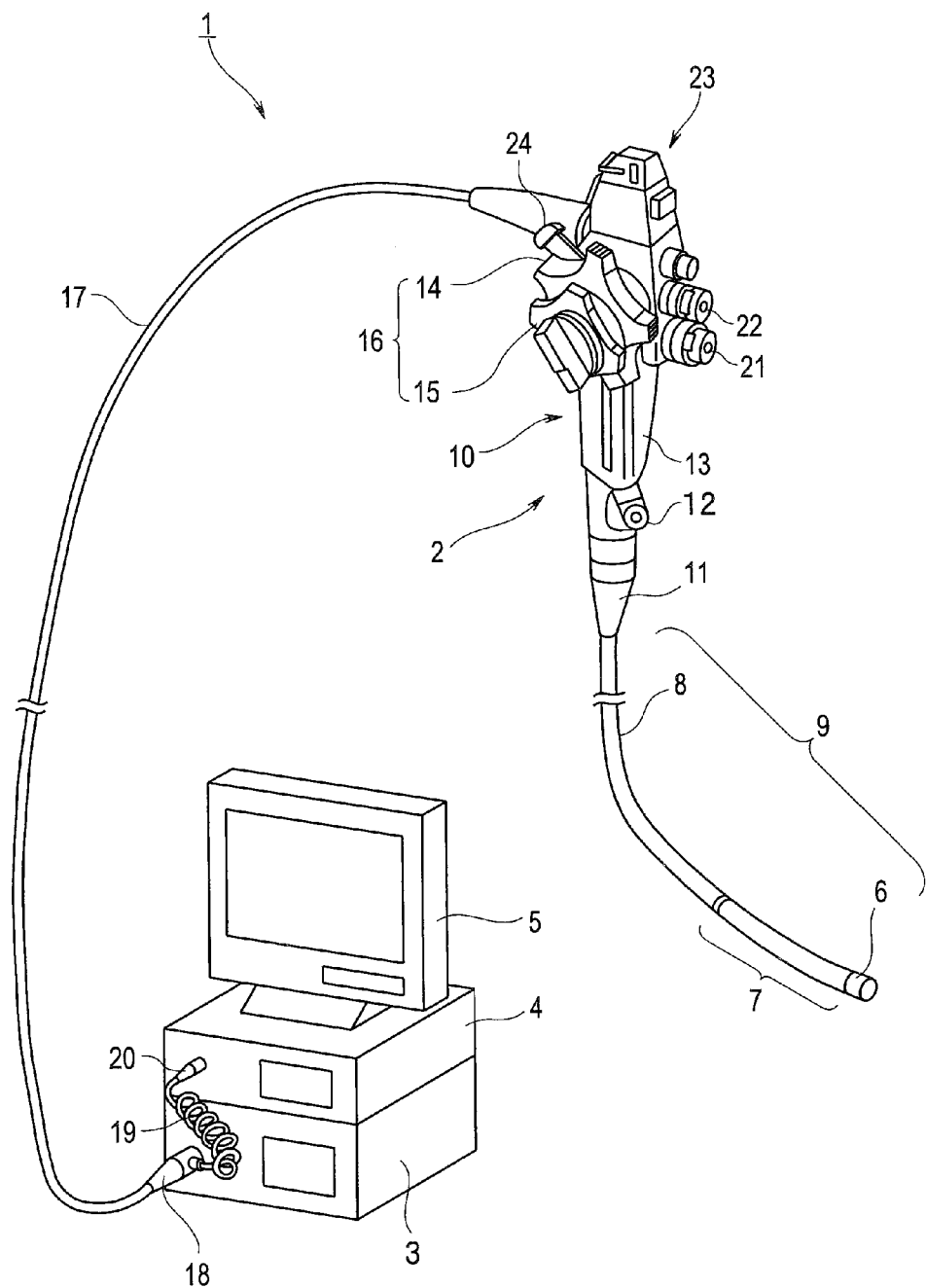
FIG. 1 is an explanatory diagram illustrating an entire configuration of an endoscope according to an aspect of the present invention.
Figure 2:
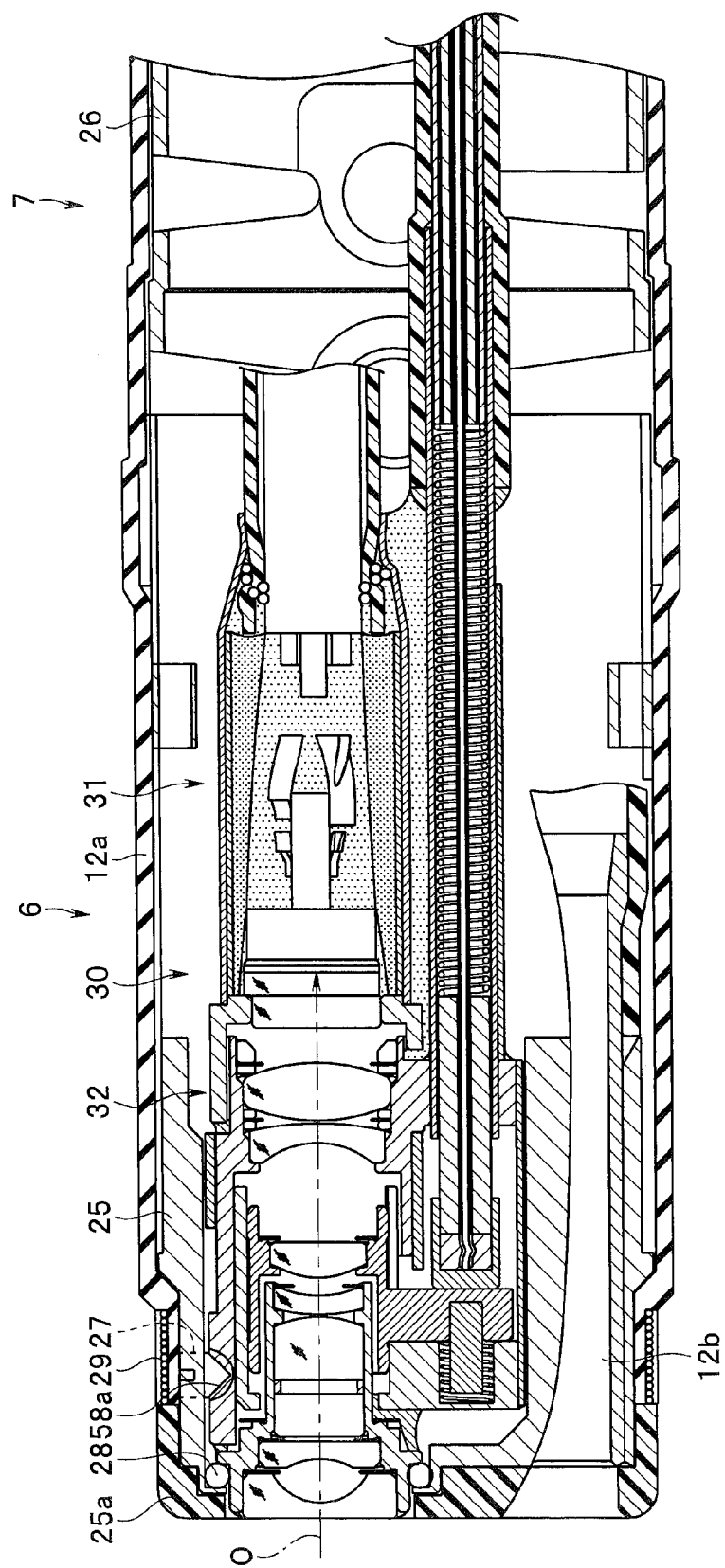
FIG. 2 is a cross-sectional diagram illustrating an internal configuration of a distal end portion and a bending portion according to the aspect of the present invention.
Figure 3:
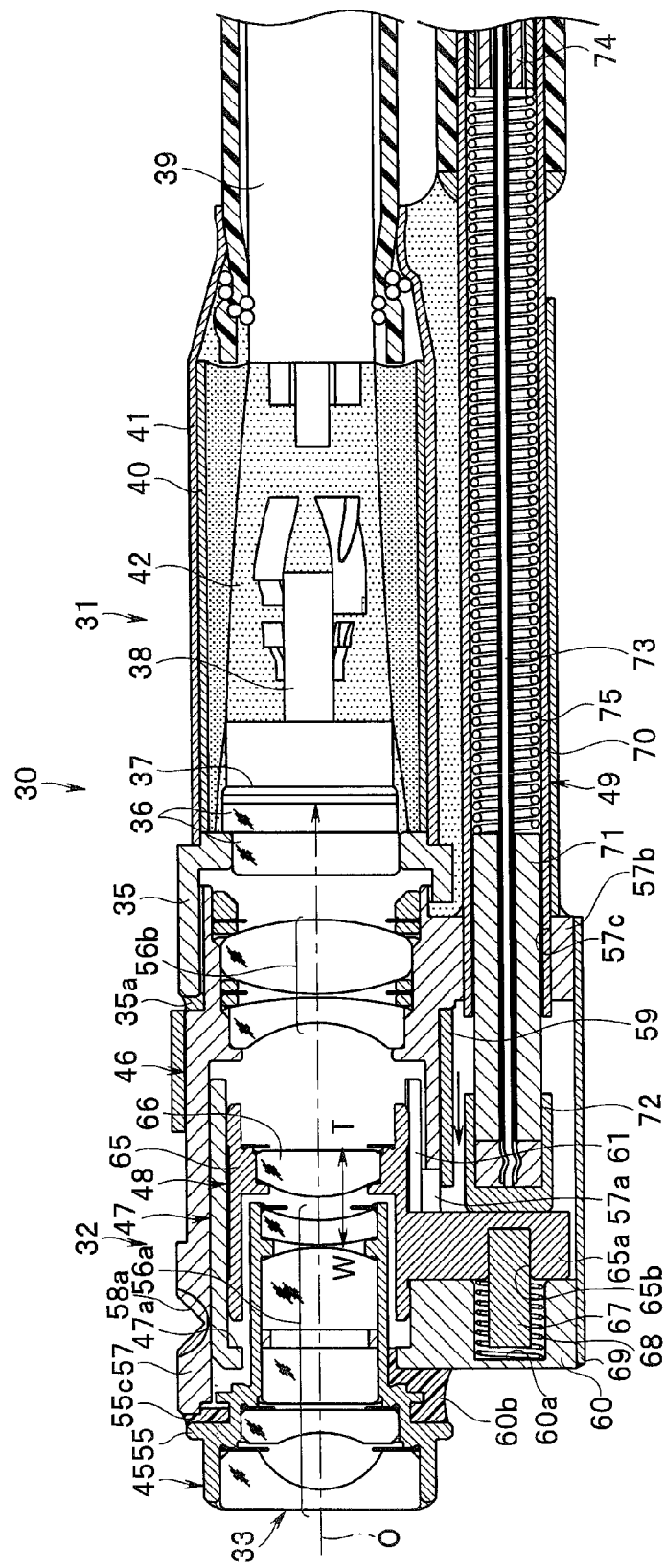
FIG. 3 is a cross-sectional diagram illustrating a configuration of an image pickup unit in a state in which a movable lens unit has been moved forward, according to the aspect of the present invention.
Figure 4:
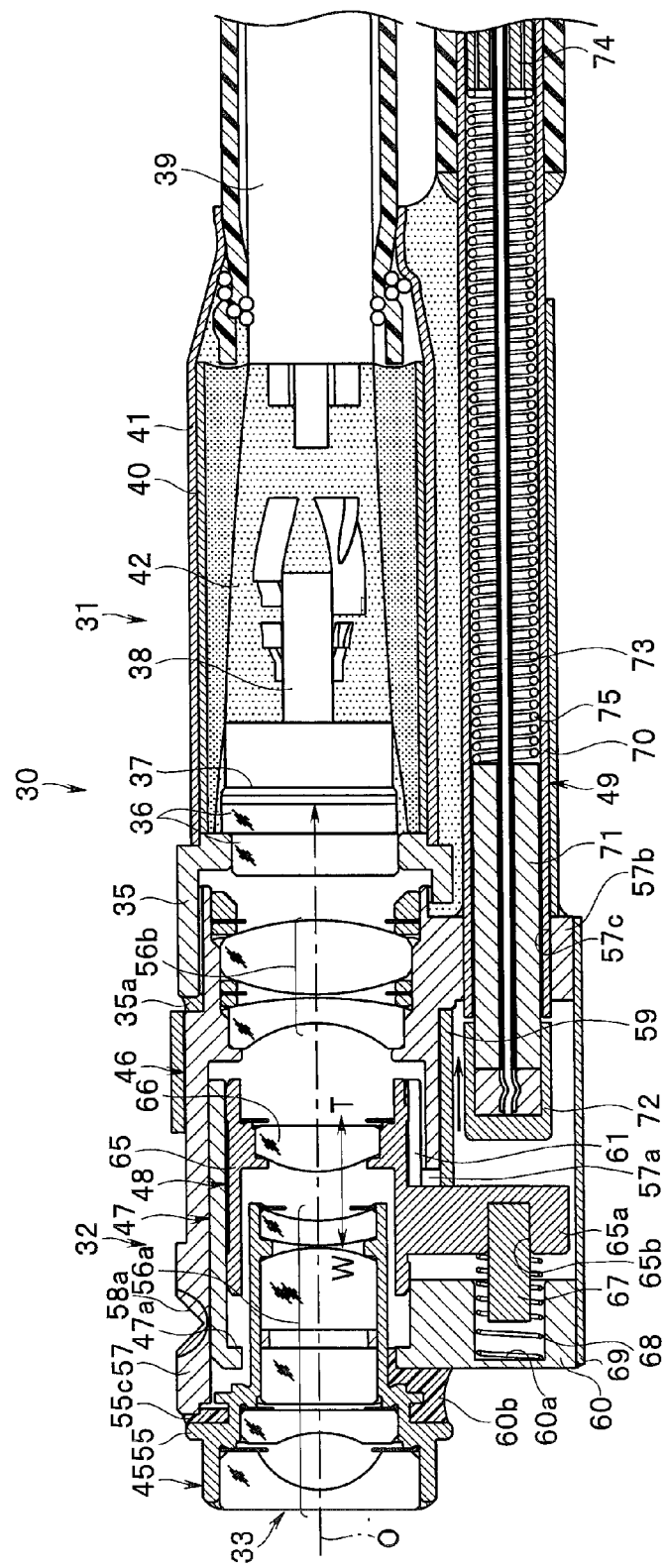
FIG. 4 is a cross-sectional diagram illustrating the configuration of the image pickup unit in a state in which the movable lens unit has been moved backward, according to the aspect of the present invention.
Figure 5:
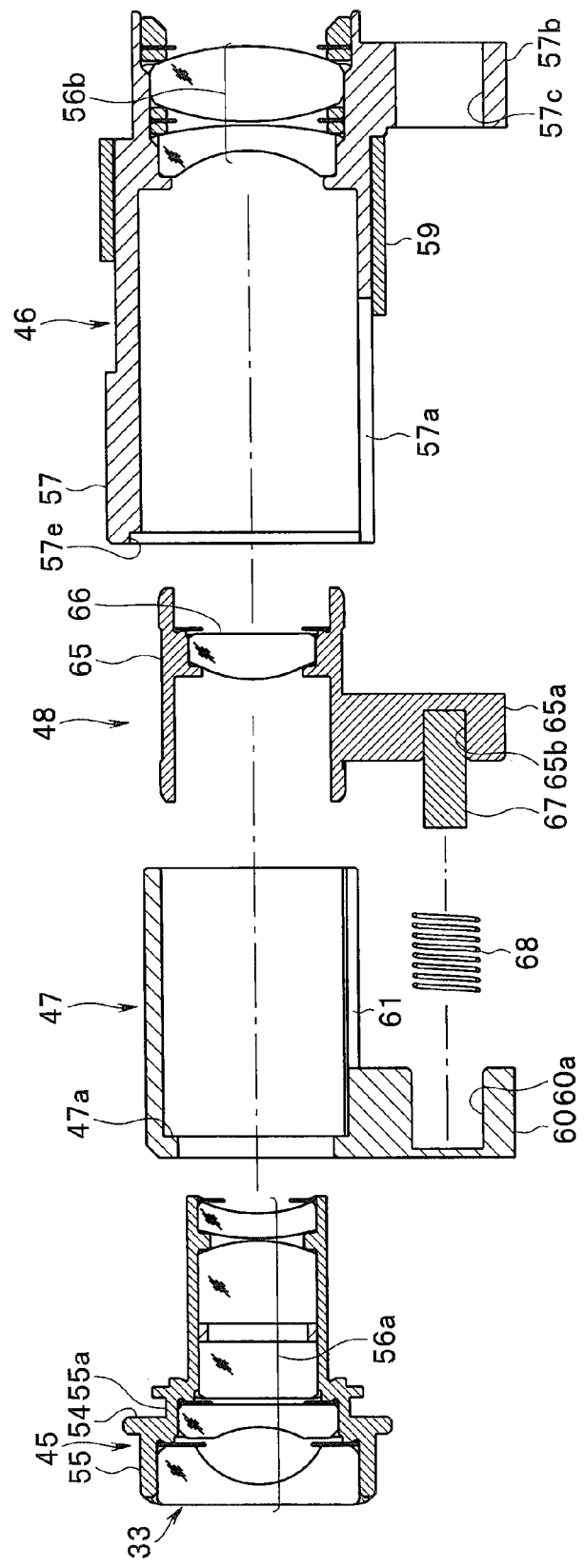
FIG. 5 is an exploded cross-sectional diagram illustrating a front group lens unit, the movable lens unit, a rear group lens unit, and a movable lens position correction frame, according to the aspect of the present invention.
Figure 6:
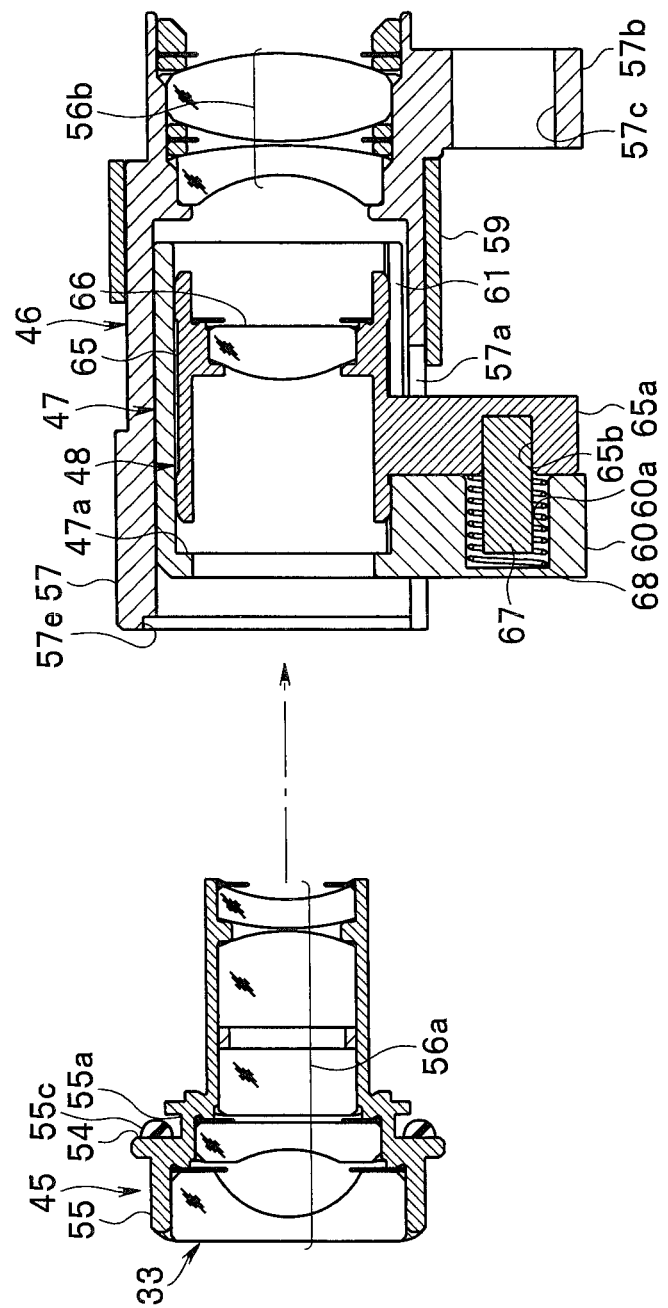
FIG. 6 is an exploded cross-sectional diagram illustrating a state before the front group lens unit is bonded and fitted to the rear group lens unit in which the movable lens unit and the movable lens position correction frame are housed, according to the aspect of the present invention.
Figure 7:
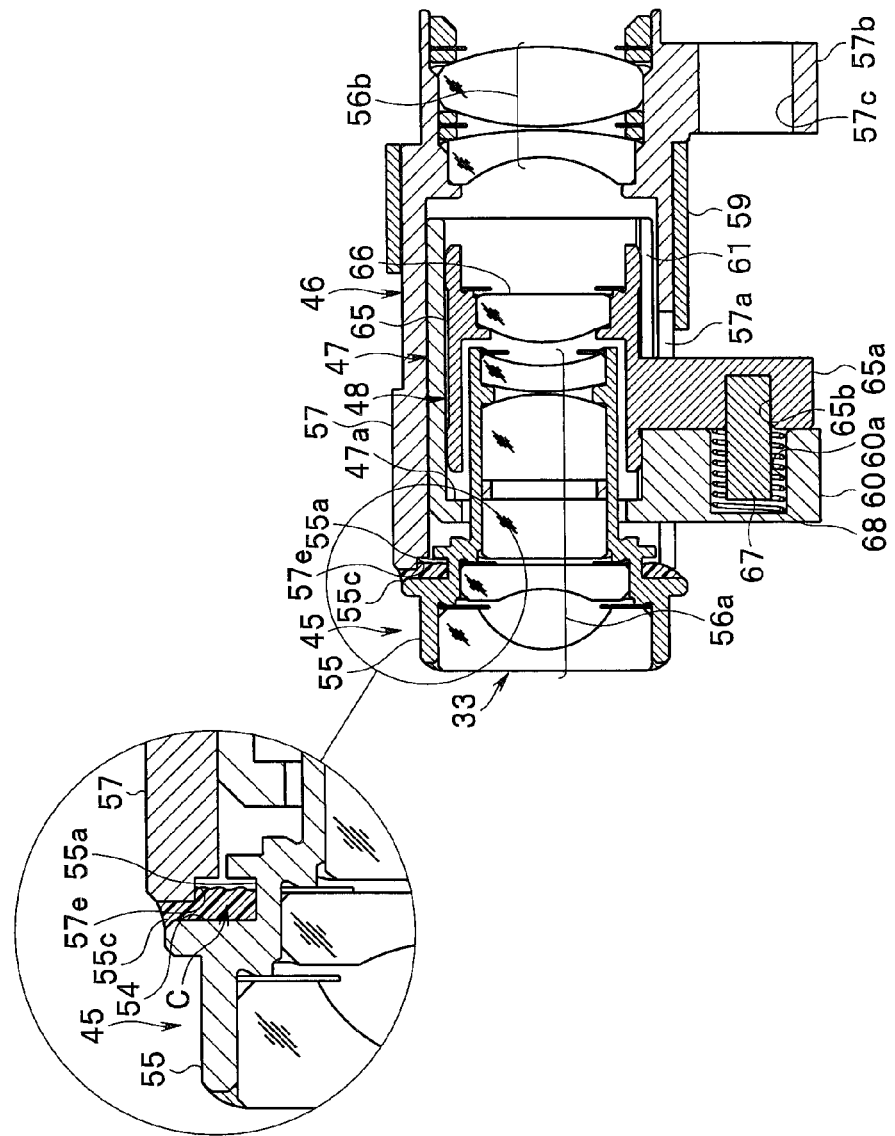
FIG. 7 is a cross-sectional diagram illustrating a state in which the front group lens unit is bonded and fitted to the rear group lens unit, according to the aspect of the present invention.

An embodiment of the present invention is described below with reference to drawings. FIG. 1 is an explanatory diagram illustrating an entire configuration of an endoscope according to an aspect of the present invention. FIG. 2 is a cross-sectional diagram illustrating an internal configuration of a distal end portion and a bending portion. FIG. 3 is a cross-sectional diagram illustrating a configuration of an image pickup unit in a state in which a movable lens unit has been moved forward. FIG. 4 is a cross-sectional diagram illustrating the configuration of the image pickup unit in a state in which the movable lens unit has been moved backward. FIG. 5 is an exploded cross-sectional diagram illustrating a front group lens unit, the movable lens unit, a rear group lens unit, and a movable lens position correction frame. FIG. 6 is an exploded cross-sectional diagram illustrating a state before the front group lens unit is bonded and fitted to the rear group lens unit in which the movable lens unit and the movable lens position correction frame are housed. FIG. 7 is a cross-sectional diagram illustrating a state in which the front group lens unit is bonded and fitted to the rear group lens unit.

As illustrated in FIG. 1, an electronic endoscope system (hereinafter, simply referred to as an endoscope system) 1 according to the present embodiment includes an electronic endoscope apparatus (hereinafter, simply referred to as an endoscope) 2 serving as an endoscope, a light source apparatus 3, a video processor 4, and a color monitor 5 that are electrically connected to one another.

The endoscope 2 includes an insertion section 9 and an operation section 10 from which the insertion section 9 is extended, and a universal cord 17 extended from the operation section 10 is connected to the light source apparatus 3 through a scope connector 18.

In addition, a coiled scope cable 19 is extended from the scope connector 18. Further, an electric connector portion 20 is provided on the other end side of the scope cable 19, and the electric connector portion 20 is connected to the video processor 4.

The insertion section 9 includes a distal end portion 6, a bending portion 7, and a flexible tube portion 8 that are connected in order from a distal end side of the insertion section 9. A well-known distal end opening portion, an observation window, a plurality of illumination windows, an observation window cleaning opening, and an observed object cleaning opening (all not illustrated) are provided on a distal end surface of the distal end portion 6.

An image pickup unit described later is disposed inside the distal end portion 6 on rear surface side of the observation window. In addition, a distal end of an unillustrated light guide bundle is disposed on a rear surface side of the plurality of illumination windows.

The light guide bundle is insertedly disposed from the insertion section 9 into the universal cord 17 through the operation section 10, and enables illumination light to be transmitted from the light source apparatus 3 to the illumination windows when the scope connector 18 is connected to the light source apparatus 3.

The observation window cleaning opening and the observed object cleaning opening configure opening parts of two cleaning tubes not illustrated. The two cleaning tubes are inserted from the distal end portion 6 into the universal cord 17.

The cleaning tubes are connected to a cleaning tank and a compressor (both not illustrated) on the light source apparatus 3 side. Cleaning water is stored in the cleaning tank.

The operation section 10 includes: a bend preventing portion 11 from which the insertion section 9 is extended; a forceps opening 12 provided on a lower side part; an operation section body 13 configuring a middle grip portion; a bending operation portion 16 configured of two bending operation knobs 14 and 15 that are provided on upper side; an air/water feeding control portion 21; a suction control portion 22; a switch portion 23 that is configured of a plurality of switches and mainly operates an image pickup function; and an operation lever 24 that operates a movable lens forward and backward to operate, for example, a focusing function of adjusting focus or a zooming function of adjusting a magnification such as wide and tele. The movable lens is provided in the image pickup unit described later.

Note that the forceps opening 12 of the operation section 10 configures an opening portion of an unillustrated treatment instrument channel. The treatment instrument channel is mainly inserted into the insertion section 9 up to a distal end opening portion of the distal end portion 6.

Next, the configuration of the distal end portion 6 of the endoscope 2 is mainly described with reference to FIG. 2.

As illustrated in FIG. 2, an image pickup unit 30 is disposed inside the distal end portion 6.

The image pickup unit 30 is fitted to a rigid distal end hard member 25, and fixed to the distal end hard member 25 by a setscrew 27 from a side surface direction.

In addition, an O-shaped ring 28 to secure water-tightness with the distal end hard member 25 is disposed on an outer peripheral part on a distal end side of the image pickup unit 30. A distal end cover 25a that configures a distal end surface of the distal end portion 6 is bonded and fixed to a distal end of the distal end hard member 25.

Note that the distal end opening portion that is a hole portion formed in the distal end cover 25a configures the opening portion of the treatment instrument channel 12b in the distal end portion 6 as mentioned above.

Further, a plurality of bending pieces 26 that configure the bending portion 7 are connected to a proximal end side of the distal end hard member 25, and outer peripheries of the distal end hard member 25 and the bending pieces 26 are integrally covered with a distal end insertion section rubber member 12a. A distal end outer peripheral part of the distal end insertion section rubber member 12a is fixed to the distal end hard member 25 by a bobbin bonding portion 29.

Note that the members such as the cleaning tubes and the illumination light guide bundle provided on the distal end portion 6 have respective conventionally well-known configurations, and description of the configurations are accordingly omitted.

Next, a detailed configuration of the image pickup unit 30 is described with reference to FIG. 3 and FIG. 4.

As illustrated in FIG. 3, the image pickup unit 30 according to the present embodiment includes a solid-state image pickup device unit 31, and an observation optical system unit 32 that is connected to a distal end of the solid-state image pickup device unit 31.

The solid-state image pickup device unit 31 includes a solid-state image pickup device holding frame 35. The solid-state image pickup device holding frame 35 holds, through an optical member 36 such as a cover glass, a front surface side of a solid-state image pickup device chip 37 configured of, for example, a CCD or a CMOS.

Further, a multilayer substrate 38 is electrically connected to a rear surface side of the solid-state image pickup device chip 37 through an unillustrated FPC or the like.

Moreover, a plurality of communication lines that are branched from a cable 39 are connected to the multilayer substrate 38. The cable 39 is inserted into the endoscope 2, and is electrically connected to the video processor through the electric connector portion 20.

In addition, a reinforcing frame 40 is connected to a proximal end outer peripheral part of the solid-state image pickup device holding frame 35, and a heat-shrinkable tube 41 that covers up to a distal end part of the cable 39 is provided on an outer periphery of the reinforcing frame 40.

Note that a space that is formed by a proximal end part of the solid-state image pickup device holding frame 35, the reinforcing frame 40, and the heat-shrinkable tube 41 is filled with a protective agent 42 such as an adhesive that retains water-tightness of the solid-state image pickup device unit 31 and protects the solid-state image pickup device unit 31.

The observation optical system unit 32 according to the present embodiment includes a bifocal observation optical system 33. The bifocal observation optical system 33 moves an internal lens forward and backward to vary optical characteristics (a focal length), thereby achieving a focusing function or a zooming function.

More specifically, the observation optical system unit 32 includes: a front group lens unit 45 that is located on a distal end side; a rear group lens unit 46 that is connected to a proximal end of the front group lens unit 45; a movable lens position correction frame 47 that is interposed between the front group lens unit 45 and the rear group lens unit 46; a movable lens unit 48 that is movable forward and backward inside the movable lens position correction frame 47 in a photographing optical axis O direction; and an actuator 49 that moves the movable lens unit 48 forward and backward.

Note that, in the observation optical system unit 32, the solid-state image pickup device holding frame 35 of the solid-state image pickup device unit 31 is externally fitted to the rear group lens unit 46, and the rear group lens unit 46 and the solid-state image pickup device holding frame 35 are fixed to each other by an adhesive 35a.

The front group lens unit 45 includes: a front group lens frame 55 serving as a fixed frame; and a front group lens 56a configured of a plurality of fixed lenses held by the front group lens frame 55.

The rear group lens unit 46 includes: a rear group lens frame 57 serving as a fixed frame; and a rear group lens 56b configured of a plurality of fixed lenses held on the photographing optical axis O on a proximal end side of the rear group lens frame 57. A distal end of the rear group lens frame 57 is externally fitted and fixed to the front group lens frame 55 by an adhesive 55c.

The solid-state image pickup device holding frame 35 is externally fitted and fixed to the proximal end side of the rear group lens frame 57 by the adhesive 35a, which couples the solid-state image pickup device unit 31 with the observation optical system unit 32.

In addition, a slit 57a that penetrates through an inner peripheral side and an outer peripheral side of the rear group lens frame 57 is provided on the rear group lens frame 57. The slit 57a is extended in the direction same as the photographing optical axis O direction, and a distal end side of the slit 57a opens at a distal end of the rear group lens frame 57.

The rear group lens frame 57 further includes a holding rod 57b that projects in an outer diameter direction on a proximal end side of the slit 57a, and the holding rod 57b includes an actuator holding hole 57c that penetrates the holding rod 57b in a direction coaxial to the photographing optical axis O.

Note that a concave portion 58a serving as a screw receiver that receives the setscrew 27 is provided on an outer peripheral part of the rear group lens frame 57. The setscrew 27 fixes the rear group lens frame 57 to the distal end hard member 25 in a side surface direction.

Further, an adjustment ring 59 that performs stop positioning of a proximal end side of the movable lens unit 48 in the photographing optical axis O direction with high accuracy is interposed in the rear group lens frame 57.

The adjustment ring 59 is configured of a C-shaped ring member, a width in the photographing optical axis O direction of which is linearly varied along a circumferential direction. The adjustment ring 59 is disposed such that a proximal end of the adjustment ring 59 is in contact with the holding rod 57b.

Further, the adjustment ring 59 is rotated around the photographing optical axis O along an outer peripheral surface of the rear group lens frame 57, thereby changing a relative position between a movable lens frame 65 and the holding rod 57b.

As a result, the position of the movable lens frame 65 on the rear group lens frame 57 in the photographing optical axis O direction is adjusted.

The movable lens position correction frame 47 is interposed between the outer periphery side of the front group lens frame 55 and the inner periphery side of the rear group lens frame 57.

Note that the movable lens position correction frame 47 is a substantially cylindrical member that houses the movable lens frame 65 of the movable lens unit 48 and straightly guides the forward and backward movement of the movable lens frame 65. The movable lens position correction frame 47 has an outer diameter larger than an outer diameter of the middle part up to the proximal end part of the front group lens frame 55 of the front group lens unit 45 that is introduced in the rear group lens frame 57 of the rear group lens unit 46.

A front stopper 60 that projects in the outer diameter direction is provided on a distal end side of the movable lens position correction frame 47.

A spring receiving portion 60a that opens on the rear side is recessed on the front stopper 60, and a return spring 68 that is a compression spring is wound in the spring receiving portion 60a. One end of the return spring 68 is held.

A slit 61 that penetrates through an inner periphery and an outer periphery of the movable lens position correction frame 47 is provided on the movable lens position correction frame 47. The slit 61 is so extended in the direction same as the photographing optical axis O direction as to be overlapped with the slit 57*a* of the rear group lens frame 57.

A proximal end side of the slit 61 opens at the proximal end of the movable lens position correction frame 47. Note that a rib 47*a* that is extended in an inner diameter direction is provided at the distal end opening portion of the movable lens position correction frame 47.

The movable lens position correction frame 47 is to perform stop positioning of a distal end side of the movable lens unit 48 in the photographing optical axis O direction with high accuracy. The movable lens position correction frame 47 is fixed to one or both of the front group lens frame 55 of the front group lens unit 45 and the rear group lens frame 57 by an adhesive 60*b*.

The movable lens unit 48 includes: a movable lens frame 65 serving as a movable frame; and a movable lens 66 that is held by the movable lens frame 65.

In the present embodiment, the movable lens frame 65 is disposed, with the movable lens position correction frame 47 in between, inside the rear group lens frame 57 serving as a fixed frame, and is movable forward and backward in a direction along the photographing optical axis O.

An operation rod 65*a* that projects in an outer peripheral direction is provided in the movable lens frame 65. The operation rod 65*a* projects to the outer peripheral side of the rear group lens frame 57 through the slit 57*a* of the rear group lens frame 57 and the slit 61 of the movable lens position correction frame 47.

Further, the operation rod 65*a* is disposed between the front stopper 60 and the holding rod 57*b*. The operation rod 65*a* includes, on a surface facing the front stopper 60, a bearing portion 65*b* that faces the spring receiving portion 60*a*.

A shaft member 67 that projects into the return spring 68 in the spring receiving portion 60*a* is held by the bearing portion 65*b*. In addition, the operation rod 65*a* is biased toward the holding rod 57*b* on a proximal end side by biasing force of the return spring 68.

Note that a cover 69 that water-tightly closes the slits 57*a* and 61 is provided on a projection end side of the holding rod 57*b*, the front stopper 60, and the operation rod 65*a*.

The actuator 49 includes a guide tube 70, a distal end of which is held by an actuator holding hole 57*c* of the holding rod 57*b*.

A push rod 71 that is projectable and retractable from the distal end of the guide tube 70 is provided inside the guide tube 70. A head part 72 serving as a contact member that freely comes into contact with the operation rod 65*a* is fixed to a distal end of the push rod 71.

A distal end of a drive wire 73 that is inserted into the guide tube 70 is coupled to the push rod 71, and a shape-memory device 74 made of a shape-memory alloy is coupled to a proximal end of the drive wire 73.

Further, inside the guide tube 70, a push spring 75 is wound around an outer peripheral side of the drive wire 73. The push spring 75 biases the push rod 71 toward the front stopper 60 side by biasing force higher than the biasing force of the return spring 68.

For example, the shape-memory device 74 is so set as to contract when being heated and as to expand when being cooled. The shape-memory device 74 is held to be expandable and contractible inside the guide tube 70. In addition, a heat source such as an unillustrated Peltier device is provided beside the shape-memory device 74, and the heat source makes it possible to heat or cool the shape-memory device 74 in response to the operation state of the operation lever 24.

Note that the method of the shape-memory device 74 is not limited to the method of causing the shape-memory device to expand and contract by heating or cooling with use of the heat source such as the Peltier device. For example, the method of heating a shape-memory alloy by energization to cause the shape-memory alloy to contract may be adopted.

When the shape-memory device 74 expands due to cooling, the shape-memory device 74 operates the drive wire 73 in a direction releasing the biasing force of the push spring 75 (namely, in a direction toward the distal end side along the photographing optical axis O).

As a result, a distal end side of the push rod 71 projects from the guide tube 70 to press the operation rod 65*a* against the basing force of the return spring 68 that is a contraction spring.

Therefore, the operation rod 65*a* moves up to the position where the operation rod 65*a* comes into contact with the front stopper 60. The movable lens frame 65 moves the movable lens 66 up to an advance position to achieve a predetermined first focal length (for example, first optical characteristics of wide), along with the movement of the operation rod 65*a* (see FIG. 3).

In contrast, when the shape-memory device 74 contracts due to heating, the shape-memory device 74 moves the drive wire 73 in a direction against the basing force of the push spring 75 (namely, in a direction toward the proximal end side along the photographing optical axis O).

This retracts the distal end of the push rod 71 into the guide tube 70. Accordingly, the operation rod 65*a* is biased by the return spring 68 to move up to the position where the operation rod 65*a* comes into contact with the adjustment ring 59.

The movable lens frame 65 moves the movable lens 66 up to a retract position to achieve a predetermined second focal length (for example, second optical characteristics of tele) along with the movement of the operation rod 65*a* (see FIG. 4).

Here, a configuration in which the front group lens unit 45 and the rear group lens unit 46 are fitted and bonded and fixed to each other in the image pickup unit 30 having the above-described configuration is described in detail below.

As illustrated in FIG. 5 and FIG. 6, first, the movable lens position correction frame 47 and the movable lens unit 48 are previously incorporated inside the rear group lens frame 57 of the rear group lens unit 46, and the adjustment ring 59 is fitted to the outer periphery of the rear group lens frame 57.

The front group lens unit 45 is then fitted into the rear group lens unit 46 while the optical characteristics based on predetermined design values are confirmed.

At this time, the front group lens frame 55 of the front group lens unit 45 and the rear group lens frame 57 of the rear group lens unit 46 are positioned relative to each other by unillustrated jigs, and are bonded and fitted to each other.

Note that the movable lens position correction frame 47 at this time is immovably held, by an unillustrated jig or the like, at a stop position of the front side of the movable lens unit 48 that is an advance position to achieve set optical characteristics in design (for example, a wide end position in this case).

In addition, the front group lens unit 45 and the rear group lens unit 46 are held, by unillustrated jigs, in a state in which axial alignment is performed such that an optical center axis of the lens group 56a held by the front group lens unit 45 is coincident with an optical center axis of the lens group 56b held by the rear group lens unit 46 along the photographing optical axis O because lens power of the lens groups 56a and 56b are large.

The front group lens frame 55 of the front group lens unit 45 and the rear group lens frame 57 of the rear group lens unit 46 are fixed to each other by an adhesive 55c from the state.

More specifically, the front group lens frame 55 includes a concave peripheral groove 55a on an outer peripheral part on the rear side along the flat surface portion 54 of the middle part that faces a distal end surface of the rear group lens frame 57. The adhesive 55c is applied to a flat surface portion 54.

In addition, the rear group lens frame 57 includes a step-shaped peripheral groove 57e on an inner peripheral part of the distal end portion that faces the flat surface portion 54 of the front group lens frame 55.

Further, as illustrated in FIG. 7, the peripheral grooves 55a and 57e are overlapped with each other while the front group lens frame 55 and the rear group lens frame 57 are fitted to each other. This forms a hollow portion C serving as an adhesive outflow preventing portion, and excess adhesive 55c flows into the hollow portion.

In other words, the hollow portion C that is formed by the peripheral groove 55a of the front group lens frame 55 and the peripheral groove 57e of the rear group lens frame 57 becomes a so-called adhesive reservoir in which the excess adhesive 55c is housed and reserved. This prevents the excess adhesive 55c from flowing to the rear side of the front group lens frame 55.

As described above, in the image pickup unit 30 according to the present embodiment, when a large clearance is provided between the front group lens frame 55 and the rear group lens frame 57 in order to perform shift adjustment in the radial direction along with shrinkage of the pixel pitch of the solid-state image pickup device chip 37, even if the clearance is filled with a generous amount of adhesive 55c for retention of water-tightness, the excess adhesive 55c stays in the hollow portion C that is formed by the peripheral groove 55a of the front group lens frame 55 and the peripheral groove 57e of the rear group lens frame 57.

In addition, although the optical system is shortened and a bonding margin is reduced for downsizing, anchor effect by the peripheral grooves 55a and 57e makes it possible to enhance the bonding strength between the frames to a predetermined level or more, and to resist assembling load in a subsequent process and impact and load when being used by a user.

Accordingly, it is possible to prevent the adhesive 55c from flowing to the rear side of the hollow portion to fix the movable lens frame 65 of the movable lens unit 48, and to prevent the adhesive 55c from deteriorating slidability of the movable lens frame 65.

Furthermore, the movable lens position correction frame 47 may be slightly adjusted by being slid to the stop position of the front side of the movable lens unit 48 that is the appropriate advance position to achieve the optical characteristics (for example, the wide end position in this case), after the front group lens unit 45 is bonded and fitted to the rear group lens unit 46.

Therefore, since the movable lens position correction frame 47 also has the configuration that prevents the adhesive 55c from flowing to the rear side of the hollow portion C, the movable lens position correction frame 47 is slightly adjusted easily without being fixed by the adhesive 55c and being deteriorated in slidability.

Accordingly, the image pickup unit 30 according to the present embodiment makes it possible to eliminate necessity of strictly controlling the amount of the adhesive 55c when the front group lens frame 55 of the front group lens unit 45 and the rear group lens frame 57 of the rear group lens unit 46 are assembled and bonded and fixed to each other, and to improve assembling workability.

As described above, the image pickup unit 30 has the configuration that prevents fixing of the movable lens frame 65 of the movable lens unit 48 and the movable lens position correction frame 47 and prevents deterioration of slidability. In addition, the configuration makes it easy to bond and fix the front group lens frame 55 of the front group lens unit 45 to the rear group lens frame 57 of the rear group lens unit 46, thereby improving assembling workability.

Note that the hollow portion C is formed by the peripheral groove 55a of the front group lens frame 55 and the peripheral groove 57e of the rear group lens frame 57 in the above exemplification; however, the hollow portion C may be formed by any one of the peripheral groove 55a of the front group lens frame 55 and the peripheral groove 57e of the rear group lens frame 57.

Further, since the adhesive 55c is also dammed by the rib 47a that is provided in the distal end opening portion of the movable lens position correction frame 47, it is possible to prevent the adhesive 55c from fixing the movable lens frame 65 of the movable lens unit 48 and to prevent the adhesive 55c from deteriorating slidability of the movable lens frame 65.

(Modifications)

The adhesive outflow preventing portion preventing the adhesive 55c that bonds the front group lens frame 55 of the front group lens unit 45 to the rear group lens frame 57 of the rear group lens unit 46, from flowing to the rear side may be configured as various modifications described below.

(First Modification)

Figure 8:
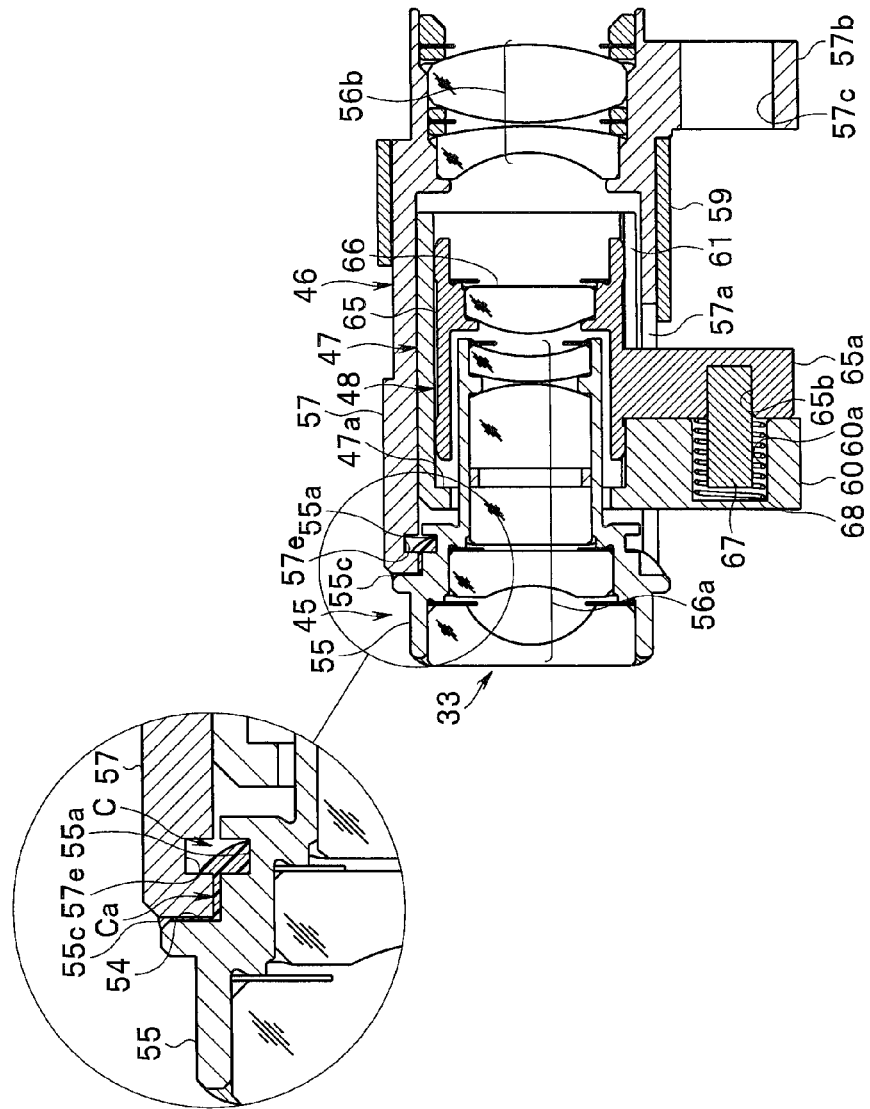
FIG. 8 is a cross-sectional diagram illustrating a state in which a front group lens unit is bonded and fitted to a rear group lens unit, according to a first modification of the aspect of the present invention.

FIG. 8 is a cross-sectional diagram illustrating a state in which a front group lens unit is bonded and fitted to a rear group lens unit according to a first modification.

As illustrated in FIG. 8, the hollow portion C serving as the adhesive outflow preventing portion may be provided at a position that is separated backward, by a predetermined distance, from the flat surface portion 54 of the front group lens frame 55 facing the distal end surface of the rear group lens frame 57.

In other words, in the present modification, the concave peripheral groove 55a of the front group lens frame 55 and the concave peripheral groove 57e of the rear group lens frame 57 are provided at respective positions that are separated backward, by a predetermined distance, from the flat surface portion 54 of the front group lens frame 55.

When the adhesive 55c flows to the rear side by so-called capillary phenomenon caused by a clearance Ca that is formed by an outer peripheral surface of the front group lens frame 55 and an inner peripheral surface of the rear group lens frame 57, such a configuration also makes it possible to cause the adhesive 55c to stay in the hollow portion C, thereby preventing the adhesive 55c from flowing out toward the movable lens frame 65 side of the movable lens unit 48 and toward the movable lens position correction frame 47 side.

Further, since the clearance Ca as an adhesive flow path at an inlet is narrow, water-tightness is enhanced by the adhesive 55c flown to the clearance Ca. In addition, since the adhesive 55c inevitably flows into the clearance Ca as the narrow adhesive flow path, it is possible to stably obtain predetermined bonding force or higher.

(Second Modification)

Figure 9:
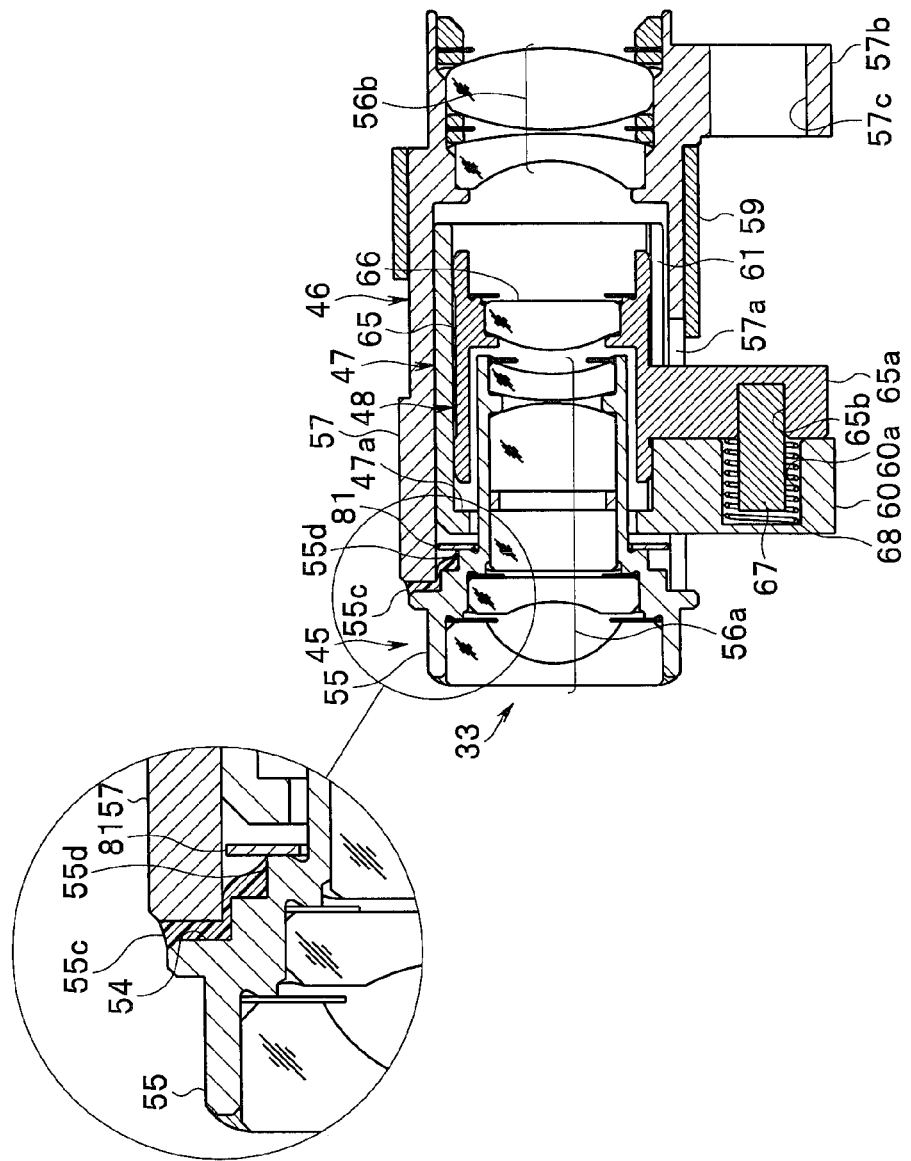
FIG. 9 is a cross-sectional diagram illustrating a state in which a front group lens unit is bonded and fitted to a rear group lens unit, according to a second modification of the aspect of the present invention.

FIG. 9 is a cross-sectional diagram illustrating a state in which a front group lens unit is bonded and fitted to a rear group lens unit according to a second modification.

As illustrated in FIG. 9, a step part 55d may be provided at a middle portion of the front group lens frame 55 in a circumferential direction, and a ring-shaped plate member 81 serving as an adhesive outflow preventing portion may be so provided as to come into contact with the step part 55d from behind of the step part 55d to prevent the adhesive 55c from flowing out toward the movable lens frame 65 side of the movable lens unit 48 and toward the movable lens position correction frame 47 side.

In other words, in the present modification, even if the excess adhesive 55c flows out to the step part 55d of the front group lens frame 55, the flow of the adhesive 55c backward is stopped by the plate member 81. As a result, the outflow of the adhesive 55c toward the movable lens frame 65 of the movable lens unit 48 and toward the movable lens position correction frame 47 is prevented.

(Third Modification)

Figure 10:
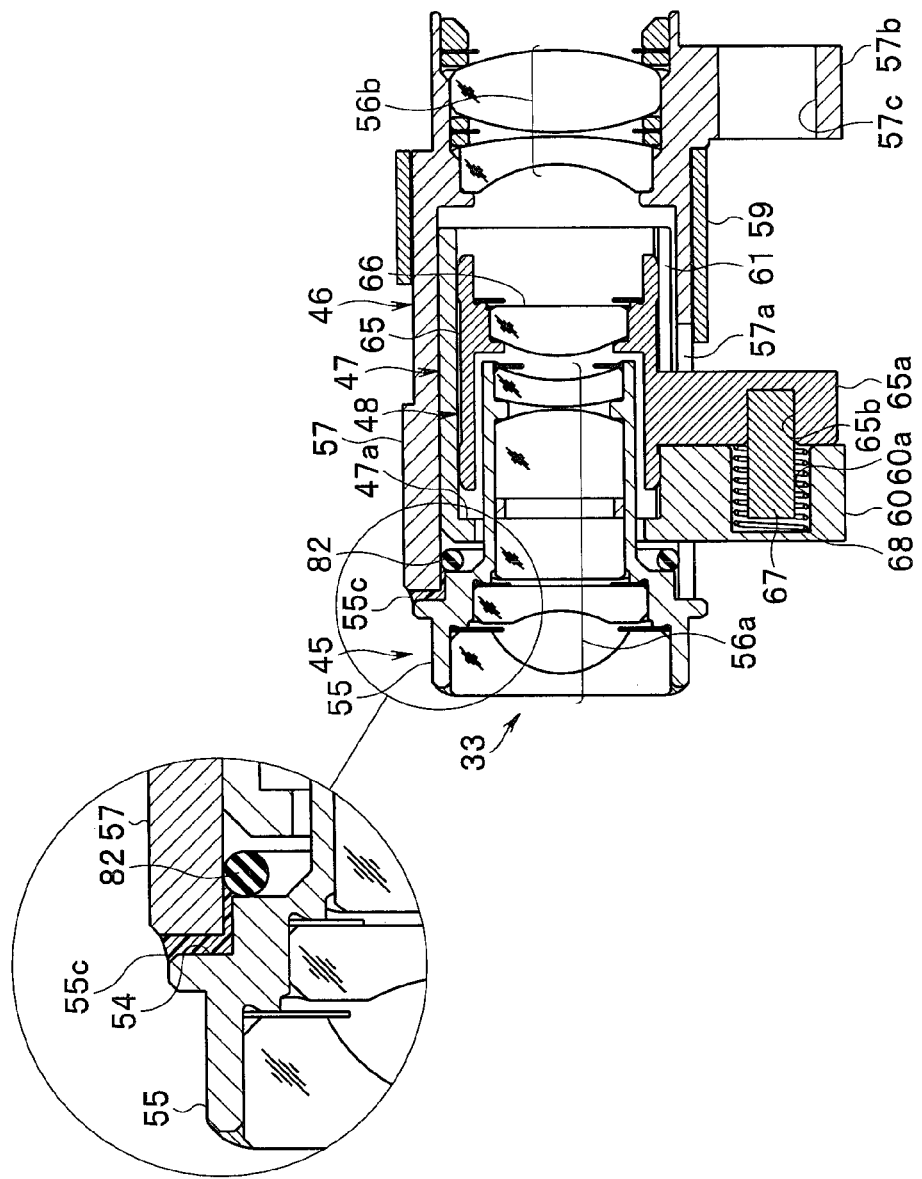
FIG. 10 is a cross-sectional diagram illustrating a state in which a front group lens unit is bonded and fitted to a rear group lens unit, according to a third modification of the aspect of the present invention.

FIG. 10 is a cross-sectional diagram illustrating a state in which a front group lens unit is bonded and fitted to a rear group lens unit according to a third modification.

As illustrated in FIG. 10, an O-shaped ring 82 serving as an adhesive outflow preventing portion that comes into contact with the inner peripheral surface of the rear group lens frame 57 may be so provided at the middle portion of the front group lens frame 55 as to block an outflow path of the adhesive 55c, thereby preventing the adhesive 55c from flowing out toward the movable lens frame 65 side of the movable lens unit 48 and toward the movable lens position correction frame 47 side.

Note that, in place of the O-shaped ring 82, using a hollow ring-shaped tube body as the adhesive outflow preventing portion enhances adhesiveness between the front group lens frame 55 and the rear group lens frame 57 because of expansion of internal air at high temperature.

Accordingly, it is possible to further prevent the adhesive 55c that has been enhanced in liquidity by high temperature, from flowing out toward the movable lens frame 65 side of the movable lens unit 48 and toward the movable lens position correction frame 47 side.

(Fourth Modification)

Figure 11:
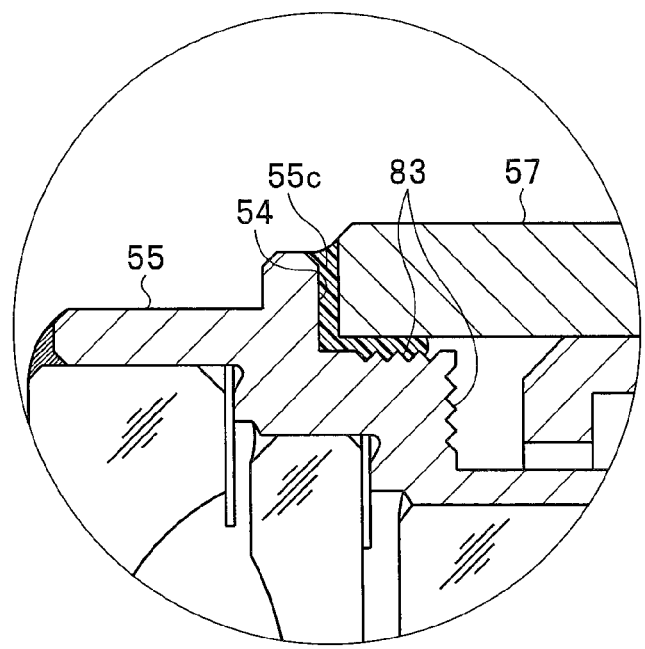
FIG. 11 is a partial cross-sectional diagram illustrating, in an enlarged manner, a state in which a front group lens unit is bonded and fitted to a rear group lens unit, according to a fourth modification of the aspect of the present invention.

FIG. 11 is a partial cross-sectional diagram illustrating, in an enlarged manner, a state in which a front group lens unit is bonded and fitted to a rear group lens unit according to a fourth modification.

As illustrated in FIG. 11, a rough surface portion 83 serving as the adhesive outflow preventing portion may be provided on a surface portion such as the outer peripheral part of the front group lens frame 55, to suppress the outflow velocity of the adhesive 55c, thereby preventing the adhesive 55c from flowing out toward the movable lens frame 65 side of the movable lens unit 48 and toward the movable lens position correction frame 47 side. The rough surface portion 83 is varied in surface roughness by being provided with screw threads or being knurled.

Note that the rough surface portion 83 may be also formed on the inner peripheral surface of the rear group lens frame 57, or may not be provided on the front group lens frame 55 but may be provided only on the rear group lens frame 57.

(Fifth Modification)

Figure 12:
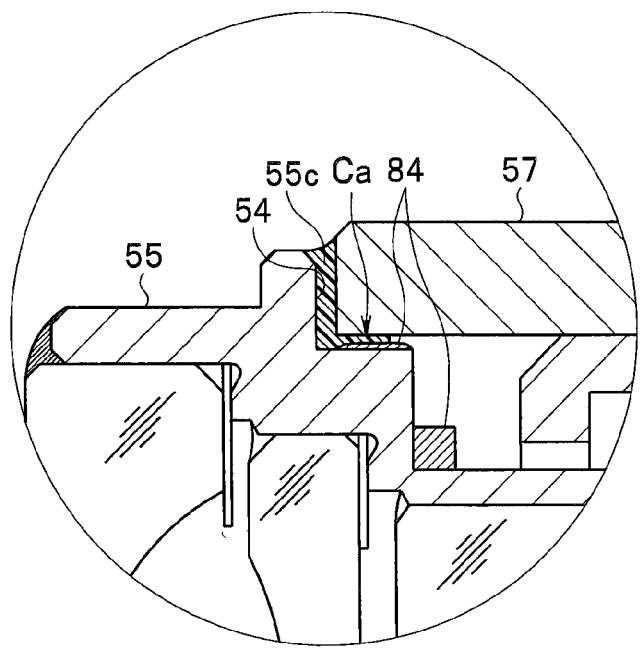
FIG. 12 is a partial cross-sectional diagram illustrating, in an enlarged manner, a state in which a front group lens unit is bonded and fitted to a rear group lens unit, according to a fifth modification of the aspect of the present invention.

FIG. 12 is a partial cross-sectional diagram illustrating, in an enlarged manner, a state in which a front group lens unit is bonded and fitted to a rear group lens unit according to a fifth modification.

As illustrated in FIG. 12, an adhesive curing acceleration region 84 serving as the adhesive outflow preventing portion may be provided in the clearance Ca between an outer peripheral surface of the front group lens frame 55 and the inner peripheral surface of the rear group lens frame 57, in the outflow path of the adhesive 55c, and the like. The adhesive curing acceleration region 84 may be a coating surface, a protrusion, or the like that contains a curing accelerator accelerating curing of the adhesive 55c.

In other words, the adhesive curing acceleration region 84 accelerates curing of the adhesive 55c, which makes it possible to prevent the adhesive 55c from flowing out toward the movable lens frame 65 side of the movable lens unit 48 and toward the movable lens position correction frame 47 side.

(Sixth Modification)

Figure 13:
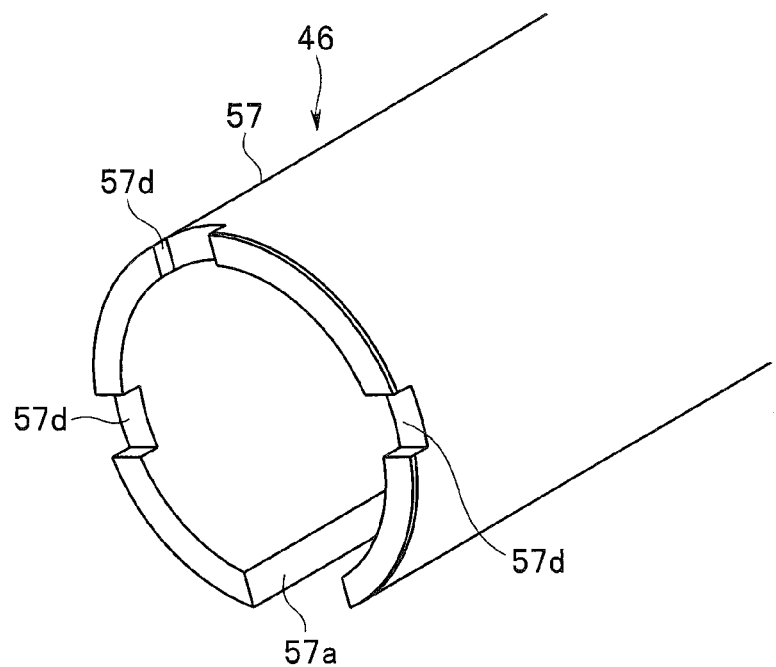
FIG. 13 is a perspective view illustrating a configuration of a rear group lens frame of a rear group lens unit according to a sixth modification of the aspect of the present invention.
Figure 14:
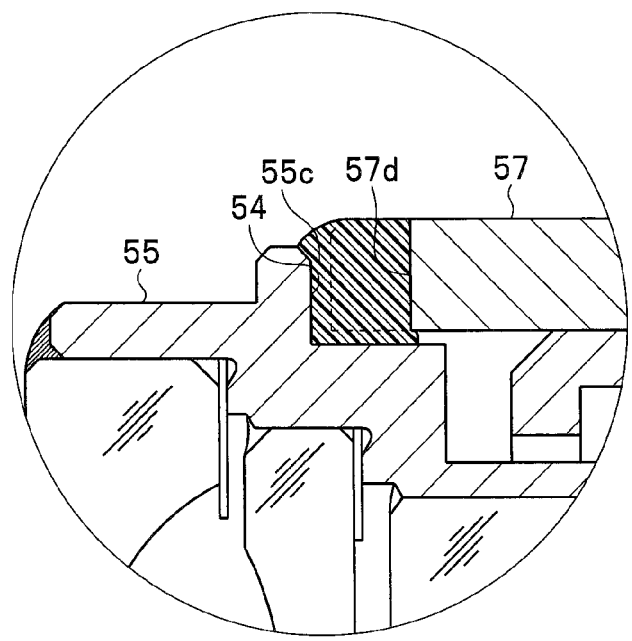
FIG. 14 is a partial cross-sectional diagram illustrating, in an enlarged manner, a state in which a front group lens unit is bonded and fitted to the rear group lens unit, according to the sixth modification of the aspect of the present invention.

FIG. 13 is a perspective view illustrating a configuration of a rear group lens frame of a rear group lens unit according to a sixth modification, and FIG. 14 is a partial cross-sectional diagram illustrating, in an enlarged manner, a state in which a front group lens unit is bonded and fitted to the rear group lens unit.

As illustrated in FIG. 13 and FIG. 14, a plurality of cutout portions 57d each serving as the adhesive outflow preventing portion may be provided on the distal end surface of the rear group lens frame 57 of the rear group lens unit 46, thereby increasing a bonding volume of the adhesive 55c later. In the modification, the cutout portions 57d are provided at an upper part and right and left parts of the distal end surface of the rear group lens frame 57 of the rear group lens unit 46.

In other words, when the front group lens frame 55 is bonded and fitted to the rear group lens frame 57, the bonding amount of the adhesive 55c is minimized to allow for visual confirmation whether quality such as watertightness is sufficiently secured.

If it is confirmed that the bonding region is insufficient due to the cutout portions 57d, it is possible to secure quality by applying a repair adhesive to the cutout portions 57d after the front group lens frame 55 is bonded and fitted to the rear group lens frame 57.

Since such a configuration makes it possible to minimize an application amount of the adhesive 55c that bonds the front group lens frame 55 to the rear group lens frame 57, it is possible to prevent the adhesive 55c from flowing out toward the movable lens frame 65 side of the movable lens unit 48 and toward the movable lens position correction frame 47 side.

Note that, when excess adhesive 55c occurs, the adhesive 55c stays in the cutout portions 57d, which makes it possible to prevent the adhesive 55c from flowing out toward the movable lens frame 65 side of the movable lens unit 48 and toward the movable lens position correction frame 47 side as well.

(Seventh Modification)

Figure 15:
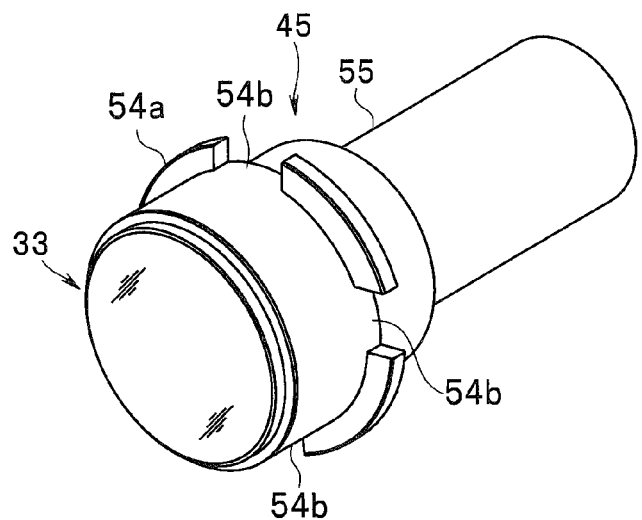
FIG. 15 is a perspective view illustrating a configuration of a front group lens frame of a front group lens unit according to a seventh modification of the aspect of the present invention.
Figure 16:
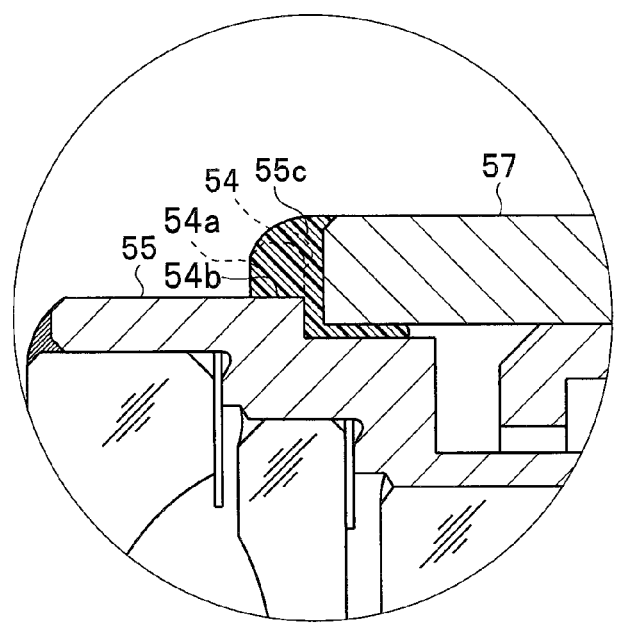
FIG. 16 is a partial cross-sectional diagram illustrating, in an enlarged manner, a state in which the front group lens unit is bonded and fitted to a rear group lens unit, according to the seventh modification of the aspect of the present invention.

FIG. 15 is a perspective view illustrating a configuration of a front group lens frame of a front group lens unit according to a seventh modification, and FIG. 16 is a partial cross-sectional diagram illustrating, in an enlarged manner, a state in which the front group lens unit is bonded and fitted to a rear group lens unit.

As illustrated in FIG. 15 and FIG. 16, a plurality of cutout portions 54b each serving as the adhesive outflow preventing portion may be provided on an outward flange portion 54a, thereby increasing a bonding volume of the adhesive 55c later, as with the sixth modification. The outward flange portion 54a forms the flat surface portion 54 on the front group lens frame 55 of the front group lens unit 45. In the modification, the cutout portions 54b are provided at an upper and lower part and right and left parts of the outward flange portion 54a.

Also in this case, when the front group lens frame 55 is bonded and fitted to the rear group lens frame 57, the bonding amount of the adhesive 55c is minimized to allow for visual confirmation whether quality such as water-tightness is sufficiently secured.

In addition, if it is confirmed that the bonding region is insufficient due to the cutout portions 54b, it is possible to secure quality by applying a repair adhesive to the cutout portions 54b after the front group lens frame 55 is bonded and fitted to the rear group lens frame 57.

Also in this case, since such a configuration makes it possible to minimize an application amount of the adhesive 55c, it is possible to prevent the adhesive 55c from flowing out toward the movable lens frame 65 side of the movable lens unit 48 and toward the movable lens position correction frame 47 side.

Further, when excess adhesive 55c occurs, the adhesive 55c stays in the cutout portions 54b, which makes it possible to prevent the adhesive 55c from flowing out toward the movable lens frame 65 side of the movable lens unit 48 and toward the movable lens position correction frame 47 side as well.

Note that the present invention is not limited to the embodiment and the modifications described above. Various modifications and alternations may be performed and are within the technical scope of the present invention. For example, the configurations of the embodiment and the modifications described above may be appropriately combined as a matter of course.

In addition, the example in which the image pickup unit is applied to the endoscope has been described in the above-described embodiment and the like; however, the present invention is not limited to such an application. The image pickup unit is applicable to other electronic apparatuses and the like as a matter of course.

The image pickup unit and the endoscope according to the present invention make it possible to prevent fixing of the movable lens frame and deterioration of slidability, and make it easy to bond and fix the front group lens frame to the rear group lens frame to improve assembling workability.

What is claimed is:

1. An image pickup unit, comprising:
a front group lens frame holding a front group lens;
a rear group lens frame fitted to the front group lens frame and holding a rear group lens;
a correction frame fixed within the rear group lens frame;
a movable frame disposed to be movable forward and backward in a direction along a photographing optical axis within the correction frame, and holding a movable lens;
a stopper provided in the correction frame, the stopper restricting movement of the movable frame in one direction of the photographing optical axis by coming into contact with the movable frame, to achieve one of focal lengths of an observation optical system;
an adhesive bonding the front group lens frame to the rear group lens frame; and
an adhesive outflow preventing portion preventing the adhesive from flowing out toward the movable frame side.

2. The image pickup unit according to claim 1, wherein the adhesive outflow preventing portion is a peripheral groove formed on an outer peripheral part of the front group lens frame and/or an inner peripheral surface of the rear group lens frame.

3. The image pickup unit according to claim 1, wherein the adhesive outflow preventing portion is a ring-shaped plate member disposed to come into contact with a step part from behind, the step part being provided on an outer peripheral part of the front group lens frame.

4. The image pickup unit according to claim 1, wherein the adhesive outflow preventing portion is an O-shaped ring provided in contact with an inner peripheral surface of the rear group lens frame to close an outflow path of the adhesive toward the movable frame side.

5. The image pickup unit according to claim 1, wherein the adhesive outflow preventing portion is a rough surface portion formed on an outer peripheral part of the front group lens frame and/or an inner peripheral surface of the rear group lens frame.

6. The image pickup unit according to claim 1, wherein the adhesive outflow preventing portion is an adhesive curing acceleration region provided on an outflow path of the adhesive toward the movable frame side.

7. The image pickup unit according to claim 1, wherein the adhesive outflow preventing portion is a cutout portion formed on a distal end surface of the rear group lens frame.

8. The image pickup unit according to claim 1, wherein the adhesive outflow preventing portion is a cutout portion formed on an outward flange portion of the front group lens frame.

9. An endoscope comprising the image pickup unit according to claim 1, at a distal end portion of an insertion section inserted in a subject.

* * * * *